(12) United States Patent
Petito

(10) Patent No.: US 9,585,943 B2
(45) Date of Patent: Mar. 7, 2017

(54) COMPOSITION FOR TISSUE/CELL REPAIR

(71) Applicant: George D. Petito, Bethlehem, PA (US)

(72) Inventor: George D. Petito, Bethlehem, PA (US)

(*) Notice: Subject to any disclaimer, the term of this patent is extended or adjusted under 35 U.S.C. 154(b) by 0 days.

(21) Appl. No.: 15/098,227

(22) Filed: Apr. 13, 2016

(65) Prior Publication Data

US 2016/0220645 A1 Aug. 4, 2016

Related U.S. Application Data

(63) Continuation-in-part of application No. 14/547,122, filed on Nov. 18, 2014.

(60) Provisional application No. 61/935,073, filed on Feb. 3, 2014.

(51) Int. Cl.
| | |
|---|---|
| *A61K 38/39* | (2006.01) |
| *A61K 35/20* | (2006.01) |
| *A61K 38/01* | (2006.01) |
| *A61K 45/06* | (2006.01) |
| *A61K 8/60* | (2006.01) |
| *A61K 8/65* | (2006.01) |
| *A61K 8/73* | (2006.01) |
| *A61Q 19/00* | (2006.01) |
| *A61Q 19/08* | (2006.01) |
| *A61K 31/381* | (2006.01) |
| *A61K 31/726* | (2006.01) |
| *A61K 31/737* | (2006.01) |
| *A61K 35/60* | (2006.01) |
| *A61K 38/00* | (2006.01) |

(52) U.S. Cl.
CPC .............. *A61K 38/39* (2013.01); *A61K 8/60* (2013.01); *A61K 8/65* (2013.01); *A61K 8/73* (2013.01); *A61K 31/381* (2013.01); *A61K 31/726* (2013.01); *A61K 31/737* (2013.01); *A61K 35/60* (2013.01); *A61K 38/014* (2013.01); *A61K 38/018* (2013.01); *A61K 45/06* (2013.01); *A61Q 19/00* (2013.01); *A61Q 19/08* (2013.01)

(58) Field of Classification Search
CPC ...... A61K 38/104; A61K 38/39; A61K 35/20; A61K 31/726; A61K 31/737; A61K 9/1652

See application file for complete search history.

(56) References Cited

U.S. PATENT DOCUMENTS

| | | | |
|---|---|---|---|
| 5,073,378 A | 12/1991 | Shoshan et al. | |
| 5,698,228 A * | 12/1997 | Takai | A61K 35/60 424/538 |
| 5,716,411 A | 2/1998 | Orgill et al. | |
| 5,929,050 A | 7/1999 | Petito | |
| 6,136,341 A | 10/2000 | Petito | |
| 6,203,805 B1 * | 3/2001 | Collins | A61K 8/64 424/401 |
| 7,320,797 B2 | 1/2008 | Gupta | |
| 7,491,541 B2 | 2/2009 | Villanueva et al. | |
| 8,168,599 B2 | 5/2012 | Petitio et al. | |
| 2003/0035786 A1 * | 2/2003 | Hendriks | A61K 38/39 424/78.17 |
| 2003/0180337 A1 | 9/2003 | Streicher et al. | |
| 2004/0162231 A1 * | 8/2004 | Hagino | A61K 36/03 424/195.17 |
| 2005/0048008 A1 * | 3/2005 | Gupta | A61K 8/447 424/59 |
| 2008/0076112 A1 * | 3/2008 | Villanueva | G01N 33/6887 435/4 |
| 2009/0100748 A1 * | 4/2009 | Belter | C10L 1/02 44/307 |
| 2010/0173868 A1 * | 7/2010 | Petito | A61K 38/39 514/57 |
| 2011/0281351 A1 * | 11/2011 | Adachi | A61L 27/3633 435/373 |
| 2013/0108700 A1 | 5/2013 | Nguyen et al. | |

* cited by examiner

*Primary Examiner* — Anand Desai
*Assistant Examiner* — Samuel Liu
(74) *Attorney, Agent, or Firm* — Richard C. Litman

(57) ABSTRACT

The composition for tissue/cell repair facilitates healing of damaged tissues, promoting tissue and cell growth, protecting cells and tissues, and reducing scar tissue. The composition includes hydrolyzed collagen, and may include high molecular weight hydrolyzed collagen. The hydrolyzed collagen may be combined with native collagen and/or at least one other therapeutic agent. For example, the therapeutic agent may be a polysulfated glycosaminoglycan, a glucosamine salt, or mixtures thereof. The collagen may be derived from two or more different sources, and may be combined with hydrolyzed whey and/or elastin.

2 Claims, No Drawings

COMPOSITION FOR TISSUE/CELL REPAIR

CROSS-REFERENCE TO RELATED APPLICATION

This application is a continuation-in-part of U.S. application Ser. No. 14/547,122, filed Nov. 18, 2014 (now pending), which claims the benefit of U.S. Provisional Patent Application Ser. No. 61/935,073, filed Feb. 3, 2014.

BACKGROUND OF THE INVENTION

1. Field of the Invention

The present invention relates to wound healing, and particularly to a method and composition for tissue/cell repair in animals or humans that provides for administering a composition comprising hydrolyzed collagen as the basic ingredient to promote wound healing, bacteriostasis, and scar reduction.

2. Description of the Related Art

Just as nature has provided the skin as a barrier for protection, it has also provided mechanisms for skin repair. Depending upon the nature of the injury, this repair process may take hours, days, months, or even years. Many factors determine the length of time it takes for injured skin to heal. Pathogenic contaminants may enter the body through the wound until the skin's integrity is restored. For this reason, it is desirable to heal open wounds as quickly as possible.

Open wounds in the skin are a potential gateway for infectious or contaminating material to enter the body. The skin is a protective barrier to external contaminants. When the skin is damaged with an open breach, these contaminants are free to enter the body. Once inside the body, these contaminants may have effects of varying degrees, but almost always become more difficult to treat, and consequently slow the process of healing the original wound.

In order to fight infection, wound management traditionally involves an initial cleansing of the affected area to remove any contaminants, such as dirt, clothing particles, or other debris. Damaged tissue and foreign materials are removed when necessary, and antiseptic agents are applied to sterilize the injured area. Sterile dressings are often applied, and are periodically changed to keep the injured area as clean and sterile as possible. Complex biological mechanisms occur during the healing process, such as chemical signals attracting fibroblast cells to the wound site, which ultimately generate connective structures, mainly of collagen. Endothelial cells generate new blood capillaries that nurture the new growth. Cell growth continues until the open wound is filled by forming permanent new tissue.

Traditional methods of wound healing have disadvantages, such as incomplete pigment removal, non-selective tissue destruction, and unsatisfactory cosmetic results, such as atrophic or hypertrophic scarring.

Thus, a method and composition for tissue/cell repair solving these problems is desired.

SUMMARY OF THE INVENTION

The method and composition for tissue/cell repair facilitates healing of damaged tissues, promoting tissue and cell growth, protecting cells and tissues, and reducing scar tissue. The composition includes proteinaceous amino acids, such as native collagen and/or hydrolyzed collagen. In some applications, the composition includes high molecular weight hydrolyzed collagen. In some embodiments, hydrolyzed collagen may be combined with native collagen, further sources of amino acids, and/or at least one other therapeutic agent. For example, further sources of amino acids may include gelatins, whey, or hydrolyzed whey and the therapeutic agent may be a polysulfated glycosaminoglycan, a glucosamine salt, or mixtures thereof.

These and other features of the present invention will become readily apparent upon further review of the following specification.

DETAILED DESCRIPTION OF THE PREFERRED EMBODIMENTS

The present composition for tissue/cell repair includes proteinaceous amino acids, such as native collagen and/or hydrolyzed collagen, which may facilitate tissue and cell growth, as well as wound healing. Hydrolyzed collagen is a collagen hydrolysate polypeptide having a molecular weight lower than native collagen. Hydrolyzed collagen may be obtained by hydrolysis of native collagen. This may be accomplished by one of four methods: (1) alkaline hydrolysis; (2) enzymatic hydrolysis; (3) acid hydrolysis; and (4) synthetically, by fermentation. Any of these methods can be used to derive the hydrolyzed collagen from a collagen source.

In addition to native collagen and/or hydrolyzed collagen, the proteinaceous amino acids can include whey and/or hydrolyzed whey. The native collagen and the hydrolyzed collagen can be derived from any suitable collagen source. The collagen source can be, for example, a bovine (skin and tendon preferred), a porcine, a reptile, a marine, an avian, or a synthetic source. The collagen can be derived from a combination of two or more collagen sources, e.g., a bovine source and a marine source. The marine source can include any fish. Preferably, the marine source includes salmon, tilapia, or a combination of salmon and tilapia. The types of amino acid constituents and their sequences determine the beneficial healing qualities of hydrolyzed collagen. Hydroxylysine and hydroxyproline are amino acids found only in collagen and in no other medical protein hydrolysates. Hydroxylysine is typically found in concentrations from 0.7 to 1.2 wt. % in hydrolyzed collagen.

The native collagen and/or hydrolyzed collagen can be derived from bovine, porcine, and/or marine sources, for example. Bovine and porcine hydrolyzed collagen have high glycine, proline, hydroxyproline, and glutamic acid content. They also display hydrophilic properties. Bovine hydrolyzed collagen, for example, demonstrates strong hydrophilic properties and when used to treat wound sites demonstrates increased perfusion and epithelialization and decreased inflammatory reaction. In contrast, marine derived, i.e., marine sourced, hydrolyzed collagen has a different amino acid profile, with higher levels of aspartic acid, cysteine, glutamine, citruline, and asparagine.

While hydrolyzed collagen of any molecular weight may be used, the hydrolyzed collagen can be High Molecular Weight hydrolyzed collagen (hereinafter "HMW hydrolyzed collagen") having a molecular weight less than native collagen. For example, the HMW hydrolyzed collagen may have a molecular weight of from about 10,000 to about 300,000 Daltons, particularly from about 10,000 to about 95,000 Daltons. The present inventor has found that the cell and tissue healing properties of HMW hydrolyzed collagen, surprisingly, far exceed those of hydrolyzed collagen with lower molecular weights, i.e., less than 10,000 Daltons. In particular, HMW hydrolyzed collagen achieves bacteriostasis faster and longer than hydrolyzed collagen having a molecular weight less than 10,000 Daltons. Achieving bacteriostasis quickly and for an extended duration promotes better cell migration, and thereby accelerates recovery. Also, use of the composition may require fewer dressing changes, thereby minimizing costs for recovery. In addition, the HMW hydrolyzed collagen provides a better occlusive barrier to the injured site than hydrolyzed collagen having a molecular weight less than 10,000 Daltons. In other words, the HMW hydrolyzed collagen functions as a protective barrier and covering for forming tissues and cells, thereby further facilitating accelerated cellular repair and wound healing. Accordingly, the present composition may provide exceptional bacteriostatic and cellular repair properties.

The high molecular weight hydrolyzed collagen can be prepared by partially hydrolyzing native collagen in any suitable manner known in the art. Preferably, raw materials from one or more collagen sources are ground to a powder, enzymatically treated, fractionated, and purified to obtain high molecular weight hydrolyzed collagen. Bulk fractionation methods known in the art can be used. The raw materials can include, for example, fat, blood, tissue, and/or bone marrow from one or more collagen sources. Raw material from fish can further include, e.g., fish head and/or fins.

The present composition may include a combination of hydrolyzed collagen and native collagen. Combining native collagen with hydrolyzed collagen may enhance the bacteriostatic effects, as well as the cellular repair and wound healing properties of the composition. The different molecular weights of the native collagen and the hydrolyzed collagen in the composition may facilitate better control over absorption amount and absorption time of the composition, as well as the degradation time of the composition. For example, by varying the ratio of the native collagen to hydrolyzed collagen, various absorption rates and degradation rates may be achieved. Preferably, the composition includes a combination of HMW hydrolyzed collagen and native collagen. Soluble and/or insoluble native collagen may be used.

The composition may include about 1% by weight to about 99% by weight hydrolyzed collagen. For example, the composition may include about 10% by weight to about 85% by weight hydrolyzed collagen or about 20% by weight to about 75% by weight hydrolyzed collagen, or about 30% by weight to about 65% by weight hydrolyzed collagen. The hydrolyzed collagen is preferably HMW hydrolyzed collagen. The composition may include about 0.1% by weight to about 65% by weight of soluble or insoluble native collagen. For example, the composition may include about 2% by weight to about 45% by weight of soluble or insoluble native collagen, or about 10% by weight to about 30% by weight of soluble or insoluble native collagen. The composition may include hydrolyzed collagen cross-linked with native collagen. For example, the composition may include about 0.1% by weight to about 65% by weight insoluble or soluble native collagen crosslinked with HMW hydrolyzed collagen. Other amounts below and above these ranges may be used.

One or more additional therapeutic agents may be included in the composition to further speed the healing process, decrease scarring and increase tissue strength. Examples of suitable therapeutic agents that may be combined with the hydrolyzed collagen are glycosaminoglycans (GAGs), particularly GAGs useful for cellular repair. Antimicrobials may also be included in the composition to further enhance its bacteriostatic quality, as can antibiotics (such as tetracycline, streptomycin, and cephalosporin) and antibacterials (such as iodine, parachlorometaxylenol, and chlorhexidine gluconate or acetate). The composition may further include lipoic acid, one or more vitamins (e.g., vitamin A, vitamin B12, vitamin C, vitamin E), omega compounds or omega-3 fatty acid compounds (e.g., α-lineloic acid "ALA", eicosapentaenoic acid "EPA", docosahexaenoic acid "DHA"),), antioxidants (e.g., superoxide dismustase, glutathione peroxidase, glutathione reductase), and/or phytochemicals (e.g., zeaxanthin, lutein). Also, it has been established that hydrolyzed collagen used as a carrier in powder form, paste or a lyophilized foam has hemostatic qualities when combined with thrombin to improve healing of wounds.

Glycosaminoglycans (GAGs) are polysaccharides found in vertebrate and invertebrate animals. Several GAGs have been found in tissues and fluids of vertebrate animals. The known GAGs are chondroitin sulfate, keratin sulfate, dermatic sulfate, hyaluronic acid, heparin, and heparin sulfate. GAGs and collagen are the major structural elements of all animal tissue. Their synthesis is essential for proper repair, treatment, protection, and maintenance of all tissues.

A particularly preferred glycosaminoglycan is chondroitin sulfate, a polysulfated GAG. Chondroitin sulfate is a linear polymer occurring in several isomers, named for the location of the sulfate group. Chondroitin-4 sulfate is found in nasal and tracheal cartilages of bovines and porcines. It is also found in the bones, flesh, blood, skin, umbilical cord, and urine of these animals. Chondroitin-6 sulfate has been isolated from the skin, umbilical cord, and cardiac valves of the aforementioned animals. Chondroitin-6 sulfate has the same composition, but slightly different physical properties from the chondroitin-4 sulfate. These are the most common isomers used in the present composition. The polymers are also known as polysulfated glycosaminoglycans (PSGAGs), chondroitin polysulfate sodium, chondrin, sodium chondroitin polysulfate, and sodium chondroitin sulfate. For consistency, the term "chondroitin sulfate" will be recited for all chondroitin sulfate isomers throughout this specification. Chondroitin sulfate is involved in the binding of collagen, and is also directly involved in the retention of moisture in the tissue. These are both valuable chemical properties that aid the healing process.

Hydrolyzed collagen in combination with GAGs, specifically a PSGAG (such as chondroitin sulfate), can be useful for the prevention and treatment of wound diseases. The hydrolyzed collagen combines with a PSGAG to bond or adhere selectively to tissue, resulting in interference with and/or displacement of bacterial or other infectious agents. In addition, the combination product may exhibit anti-enzyme activity or the ability to inhibit enzyme activity.

The hydrolyzed collagen accelerates the healing process by allowing an injured tissue to repair itself by producing and remodeling more collagen and other proteoglycans (PGs). The building blocks for collagen production are the amino acids found in hydrolyzed collagen. Hyaluronic acid and other proteoglycans (PGs) provide the framework for collagen production to follow. The PGs hold water to provide an excellent environment for healing of the tissue to begin. When in the wound site, any unused collagen that was produced is simply degraded to the amino acid. The rate-limiting step in the production of collagen is the conversion of glucose to glucosamine for the production of hyaluronic acid and other glycosaminoglycans (GAGs).

In an embodiment, the composition can include mixtures of collagen from different collagen sources. For example, the composition can include bovine sourced collagen, marine sourced collagen, and whey protein. Alternatively, the composition can include bovine sourced collagen and marine sourced collagen. According to one embodiment, the proteinaceous amino acids in the composition can include bovine sourced hydrolyzed collagen, marine sourced hydrolyzed collagen, and hydrolyzed whey protein. The composition can further include elastin. Hydrolyzed whey protein offers another alternative amino acid profile, rich in glutamic acid, isoleucine, leucine, threonine, tyrosine, and valine.

Varying the source of the amino acids in the composition can control the chemotactic, hydrophilic, and cell proliferative properties of the composition. These properties may be manipulated in order to optimize the wound healing process. This optimization may adjust the timing and balance of stimulating the inflammatory and vascular systems, as well as involvement of connective tissues and epithelial cells.

For example, a heavily exudative or wet wound can be treated, at least initially, with a highly hydrophilic composition, including at least about 50% by weight bovine sourced hydrolyzed collagen (e.g., about 50% to about 60% by weight bovine sourced hydrolyzed collagen), at least about 20% by weight marine sourced hydrolyzed collagen (e.g., about 20% to about 30% by weight marine sourced hydrolyzed collagen), and up to about 30% by weight hydrolyzed whey protein (e.g., about 5% to about 30% by weight hydrolyzed whey protein). Elastin may be added to this composition (e.g., up to about 20%) during the closing phase of wound treatment to improve tensile strength and reduce scar formation. In contrast, a dry wound can be treated with at least about 50% by weight marine sourced hydrolyzed collagen, about 20% by weight or less hydrolyzed whey, about 10% by weight or less bovine sourced hydrolyzed collagen, and about 5% by weight or less elastin.

The composition can include one or more therapeutic agents, such as an antibiotic, and/or one or more additives, such as glutamine, glycosaminoclycans, zinc, alginates, cellulose, and/or honey.

These are simplified examples, as wound healing is complex and wound specific. More complicated wounds, such as diabetic wounds, are treated using customized treatment regimens. For example, a diabetic wound can initially be treated as a wet wound, but with significantly more emphasis on hydrolyzed whey in the early treatment composition. During the later closing phase of wound treatment, the composition can be shifted to up to about 40% by weight marine sourced hydrolyzed collagen, up to about 25% by weight bovine sourced hydrolyzed collagen, and up to about 5% by weight elastin.

Further examples of this wound healing composition optimized for different applications include: about 70% bovine sourced hydrolyzed collagen and about 30% marine sourced hydrolyzed collagen; about 50% bovine sourced hydrolyzed collagen, about 30% marine sourced hydrolyzed collagen, and about 20% hydrolyzed whey; about 40% bovine sourced hydrolyzed collagen, about 20% marine sourced hydrolyzed collagen, about 20% hydrolyzed whey, and about 20% elastin; about 20% bovine sourced hydrolyzed collagen, about 40% marine sourced hydrolyzed collagen, about 20% hydrolyzed whey, and about 20% elastin; about 20% bovine sourced hydrolyzed collagen, about 40% marine sourced hydrolyzed collagen, and about 40% hydrolyzed whey; and about 30% bovine sourced hydrolyzed collagen, about 30% marine sourced hydrolyzed collagen, about 30% hydrolyzed whey, and about 10% elastin. The bovine hydrolyzed collagen can have a molecular weight of about 500 Daltons to about 10,000 Daltons. The porcine hydrolyzed collagen can have a molecular weight of about 1,000 Daltons to about 15,000 Daltons. The salmon hydrolyzed collagen can have a molecular weight of about 100 Daltons to about 10,000 Daltons. The elastin can have a molecular weight of about 35,000 Daltons to about 145,000 Daltons.

The composition may be used to heal topical and/or internal wound sites. For example, the composition may be used prior to and after surgery to minimize cell damage and to expedite wound healing. The composition may be useful during surgery to foster separation of tissue to prevent adhesion formation. The composition may be used as a filler for a wound site and remain in the wound site as it heals, becoming part of the granulated tissue.

The composition may be useful for applications relating to cosmetic and plastic surgery, e.g., as a filler for lines and wrinkles formed in the skin.

The composition may take a physical form used in topical administration, such as a gel, spray, powder, paste, foam, film for incorporation in a dressing bandage, or a topically applied patch. The composition may take a physical form used in internal administration, such as an injectable liquid or an orally ingestible liquid.

The powder form will preferably have a moisture content of about 2-10 wt. % and a pH range of 5.5 to 6.5. The powder composition will have an ash content of less than 2.5 wt. % and an isotonic point of 5.0 to 6.5. In use, the powder composition may be the preferred physical form for use with irregularly shaped wounds. Tunnel wounds, flaps, and other non-conformative sites may be managed with the powder composition because it easily conforms to any shape wound, and may be applied by a poofer bottle or otherwise blown into difficult to reach wound sites. The powder is especially useful in wounds having a large amount of exudate, as the powder can absorb nearly 30 times its own weight. As the powder absorbs the exudate, a gel is formed, which completely fills the wound site, forming a mechanical barrier against bacterial infection. The powder does not exhibit the characteristic fly-away when being applied to the wound site, and administration is perfected due to the precise powder placement.

The gel form of the composition is especially useful in wounds with lesser amounts of exudate, in burns, and in surgical sites. Application of the gel can be dispensed through a tube, a syringe, or the reservoir in a topical patch. The gel can be made of about 1-75 wt. % hydrolyzed collagen and 1-99 wt. % water. It is preferable to use about 60 wt. % collagen. The gel is formed by adding sterile water to the powder. The gel has the added advantage of adding moisture to the wound site, as well as inherent bacteriostatic properties, and stays positioned where applied.

A film form of the medicament composition may be made by mixing the powdered form with deionized water under heat at 155-175° F. Cross-linking and other agents, such as humectant, propylene glycol, sorbitol, and glycerine, may be added to the mixture. A preservative (such as benzyl alcohol or paraben) can be added. The mixture is cast on a belt liner by knife on a roll coating machine to form a liquid film, which is oven-dried. The film form can also be formed by cooling the liquid solution. These films can be used for drug or other chemical delivery, especially in dental applications. Antimicrobial and other medicinal agents can also be added to the film as needed for specific applications.

The composition may be formulated as a nutritional supplement. For example, at least one of vitamin A, vitamin C, vitamin E, vitamin B12, magnesium oxide, chelated manganese, grape seed extract, zinc, an alginate, cellulose, honey, chromium picolinate, selenium, glutamine, and glycosaminoglycans can be added to the composition to produce a nutrient composition for oral intake.

It is to be understood that the present invention is not limited to the embodiments described above, but encompasses any and all embodiments within the scope of the following claims.

I claim:

1. A composition for promoting wound healing, comprising:
   about 20% to about 30% by weight marine sourced collagen;
   about 30% by weight hydrolyzed whey protein;
   about 50% to about 60% by weight bovine sourced collagen; and
   elastin.

2. A composition for promoting wound healing, comprising: about 20% to about 30% by weight marine sourced collagen; about 30% by weight hydrolyzed whey protein; about 50% to about 60% by weight bovine sourced collagen; elastin; and at least one of zinc, an alginate, cellulose, honey, and glutamine.

* * * * *